(12) United States Patent
Zheng et al.

(10) Patent No.: US 10,429,317 B2
(45) Date of Patent: Oct. 1, 2019

(54) OPTICAL DEVICE FOR DETECTING AN INTERNAL FLAW OF A TRANSPARENT SUBSTRATE AND METHOD FOR THE SAME

(71) Applicants: Yuan Zheng, Shanghai (CN); Jia Zhu, Shanghai (CN)

(72) Inventors: Yuan Zheng, Shanghai (CN); Jia Zhu, Shanghai (CN)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 0 days.

(21) Appl. No.: 15/579,064

(22) PCT Filed: May 18, 2016

(86) PCT No.: PCT/CN2016/082440
§ 371 (c)(1),
(2) Date: Dec. 1, 2017

(87) PCT Pub. No.: WO2016/192534
PCT Pub. Date: Dec. 8, 2016

(65) Prior Publication Data
US 2018/0164225 A1    Jun. 14, 2018

(30) Foreign Application Priority Data

Jun. 3, 2015  (CN) .......................... 2015 1 0301023

(51) Int. Cl.
*G01N 21/896* (2006.01)
*G01N 21/88* (2006.01)
(Continued)

(52) U.S. Cl.
CPC ....... *G01N 21/896* (2013.01); *G01N 21/8806* (2013.01); *G01N 21/8901* (2013.01);
(Continued)

(58) Field of Classification Search
CPC .......... G01N 21/896–8967; G01N 2021/8854; G01N 2021/8867
See application file for complete search history.

(56) References Cited

U.S. PATENT DOCUMENTS 4,697,082 A * 9/1987 Bartelsen ............. G01N 21/359
250/341.1
5,699,447 A * 12/1997 Alumot .................. G01N 21/94
348/126
(Continued)

FOREIGN PATENT DOCUMENTS

CN     1220730 A     6/1999
CN     1536349 A     10/2004
(Continued)

OTHER PUBLICATIONS

International Search Report dated Jul. 26, 2016 from corresponding International Application No. PCT/CN2016/082440 (4 pages).
(Continued)

*Primary Examiner* — Rebecca C Bryant
(74) *Attorney, Agent, or Firm* — Maier & Maier, PLLC (57) ABSTRACT

An optical device and a method for detecting a flaw of a transparent substrate. A first detection unit is configured to detect the substrate at a predetermined low resolution, where the first detection unit includes a first photosensitive element and a first lens between the substrate and the first photosensitive element, and the first photosensitive element and the first lens are disposed such that an object plane is inclined relative to the substrate; a second detection unit configured to detect the substrate at a predetermined high resolution, where the second detection unit includes a second photosensitive element and a second lens between the substrate and the second photosensitive element; and a processor configured to determine a portion of the flaws
(Continued)

detected by the first detection unit as flaws to be detected by the second detection unit, and to determine a type of flaw for the substrate imaged.

10 Claims, 6 Drawing Sheets

(51) Int. Cl.
*G01N 21/89* (2006.01)
*G01N 21/958* (2006.01)

(52) U.S. Cl.
CPC ....... *G01N 21/8914* (2013.01); *G01N 21/958* (2013.01); *G01N 2021/8867* (2013.01); *G01N 2021/8967* (2013.01)

(56) References Cited

U.S. PATENT DOCUMENTS

| | | | |
|---|---|---|---|
| 5,777,729 A * | 7/1998 | Aiyer | G01N 21/4788 356/237.1 |
| 5,790,247 A | 8/1998 | Henley et al. | |
| 9,310,290 B2 * | 4/2016 | Wang | G01N 21/9501 |
| 2004/0046102 A1 * | 3/2004 | Horiuchi | G02B 7/38 250/201.2 |
| 2004/0086166 A1 * | 5/2004 | Weiss | G01N 21/95607 382/141 |
| 2016/0261786 A1 * | 9/2016 | Ahn | H04N 5/23212 |

FOREIGN PATENT DOCUMENTS

| | | |
|---|---|---|
| CN | 101614680 A | 12/2009 |
| CN | 203203941 U | 9/2013 |
| CN | 104406988 A | 3/2015 |
| JP | 2008180602 A | 8/2008 |
| WO | 2005073698 A1 | 8/2005 |

OTHER PUBLICATIONS

PCT Written Opinion dated Jul. 21, 2016 from corresponding International Application No. PCT/CN2016/082440 (4 pages).

* cited by examiner

OPTICAL DEVICE FOR DETECTING AN INTERNAL FLAW OF A TRANSPARENT SUBSTRATE AND METHOD FOR THE SAME

This application claims the benefit of priority to Chinese Patent Application No. 201510301023.0 titled "OPTICAL DEVICE FOR DETECTING AN INTERNAL FLAW OF A TRANSPARENT SUBSTRATE AND METHOD FOR THE SAME", filed with the Chinese State Intellectual Property Office on Jun. 3, 2015, the entire disclosure of which is incorporated herein by reference.

FIELD

The present disclosure relates to the optical detection technology, and in particular to an optical device and a method for detecting an internal flaw of a transparent substrate.

BACKGROUND

A variety of flaws may be induced in manufacturing flat glass. Flaws typically include internal flaws such as bubbles, stones, knots and the like, as well as surface flaws such as sticky dirt, scratches, tin points and the like. Among these flaws, the glass manufacturer generally focuses more on the internal flaws due to the larger security risks of the internal flaws.

CN1220730 discloses a method for detecting flaws, including taking photos of each portion of the glass firstly, and then enlarging the local images and identifying the types of the flaws by observing the enlarged images. However, the method relies on manual inspection, and at least a majority of the flaws have to be observed in the enlarged images, which leads to a low efficiency and cannot meet the real-time quality control on the production line.

Most of the real-time detection devices for the glass production lines are based on line scan cameras with different illumination modules. For example, it is proposed in U.S. Pat. No. 5,790,247A a method for identifying surface flaws and internal flaws. This method involves two illumination modules, namely, an internal side illumination and an external front side illumination. The two light sources illuminate the flaws in different ways to identify dusts and the internal flaws.

These real-time detection devices distinguish a surface flaw from an internal flaw based on the difference between the images for a surface flaw and an internal flaw imaged in different illumination modes. Since images for all or most of the flaws imaged in multiple illumination modes are required and the images has to be compared, the efficiency and accuracy of the detection cannot meet the requirement.

Therefore, a device and a method for detecting an internal flaw of a transparent substrate is desirable, which can achieve a high efficiency and accuracy of the detection.

SUMMARY

In an aspect, an optical device for detecting an internal flaw of a transparent substrate is provided according to an embodiment of the present disclosure. The optical device includes a first detection unit configured to detect the substrate at a predetermined low resolution. The first detection unit includes a first photosensitive element and a first lens between the substrate and the first photosensitive element. The first photosensitive element and the first lens are disposed such that an object plane is inclined relative to the substrate. The optical device further includes: a second detection unit configured to detect the substrate at a predetermined high resolution, where the second detection unit includes a second photosensitive element and a second lens between the substrate and the second photosensitive element; and a processor configured to determine a portion of the flaws detected by the first detection unit as flaws to be detected by the second detection unit, and to determine a type of the flaw based on an image for the substrate imaged by the second detection unit.

Since the optical device detects at a low resolution and a high resolution respectively, the optical device has a relatively high detection efficiency and a relatively low cost.

Specifically, the processor determines only a portion of the flaws detected by the first detection unit as flaws to be detected by the second detection unit, thereby avoiding identifying the details of all the detected flaws one by one to determine the types of the flaws. Therefore, the optical device has a relatively high detection efficiency.

Furthermore, since the substrate is detected at a low resolution firstly, a photosensitive element with fewer number of pixels may be used to ensure the width of the whole substrate (the width direction is approximately perpendicular to the longitudinal direction along which the substrate moves relative to the camera) being covered by the field of view. Therefore, the optical device has a relatively low cost.

Further, the first photosensitive element and the first lens for detecting at the low resolution are disposed such that an object plane is inclined relative to the substrate. This arrangement allows flaws at different positions of the substrate in the thickness direction to be imaged by the first detection unit. Therefore, in the low-resolution detection, it is only required that the photosensitive element moves relative to the substrate in the longitudinal direction, and it is not necessary for the photosensitive element to move relative to the substrate in a thickness direction to find out flaws at different positions of the substrate in the thickness direction. The detection efficiency is further improved.

Moreover, the magnification of the first detection unit may be set lower or the pixel size of the first photosensitive element may be set larger in the low-resolution detection. The beneficial effect brought by the above set is that a depth of field (DOF) of the first detection unit is increased, thereby allowing the substrate to move relative to the photosensitive element at a faster speed without missing a certain flaw between two frames of images imaged at two successive time instants. The detection efficiency is further improved.

In an embodiment, the magnification of the second detection unit may be higher than the magnification of the first detection unit, and a construction of the second photosensitive element may be the same as a construction of the first photosensitive element, i.e., the resolution of the detection may be changed by replacing the lens or changing the position of the lens.

In an embodiment, a pixel size of the second photosensitive element may be smaller than a pixel size of the first photosensitive element, and a construction of the second lens may be the same as a construction of the first lens, i.e., the resolution of the detection may be changed by replacing the photosensitive element.

In an embodiment, the second photosensitive element and the second lens may be disposed such that an object plane is inclined relative to the substrate.

In an embodiment, the first photosensitive element and the second photosensitive element may include a CCD sensor or a CMOS sensor.

In an embodiment, the processor may be configured to: determine a position of the flaw in the substrate in the thickness direction based on a position of a pixel where the flaw is imaged on the first photosensitive element when the image for the flaw imaged by the first detection unit has an optimum sharpness, so as to determine whether the flaw is a flaw to be detected by the second detection unit.

In an embodiment, the processor may be configured to: acquire a sequence of images for one flaw imaged by the first detection unit, the sequence of images including at least three images imaged at three successive time instants respectively, where a sharpness value of the image imaged at an intermediate time instant is higher than sharpness values of the images imaged at the other two time instants; and determine the image imaged at the intermediate time instant as the image for the one flaw with an optimum sharpness imaged by the first detection unit.

In an embodiment, the substrate may be glass.

In another aspect, a method for detecting an internal flaw of a transparent substrate is provided according to an embodiment of the present disclosure, the method includes:

a. disposing a photosensitive element and a lens such that an object plane is inclined relative to the substrate;

b. detecting the substrate at a predetermined low resolution;

c. determining a portion of the flaws detected at the predetermined low resolution as flaws to be detected at a predetermined high resolution; and d. determining a type of the flaw based on an image for the substrate imaged at the predetermined high resolution.

The summary of the present disclosure is not intended to describe each disclosed embodiment or each implementation of the present disclosure. The following detailed description and the accompanying drawings more specifically illustrate exemplary embodiments of the present disclosure.

BRIEF DESCRIPTION OF THE DRAWINGS

Throughout the accompanying drawings, like reference numerals should be understood to represent the same, similar or corresponding features or functions. The elements of the drawings are not necessarily to scale relative to each other for convenience of the illustration.

DETAILED DESCRIPTION OF EMBODIMENTS

In the following detailed description of the preferred embodiments, reference is made to the accompanying drawings that form a part of the present disclosure. The accompanying drawings show, by way of illustration, specific embodiments in which the present disclosure may be practiced. The illustrated embodiments are not intended to be exhaustive of all embodiments according to the present disclosure. It is to be understood that other embodiments may be utilized and structural or logical changes may be made without departing from the scope of the present disclosure. The following detailed description, therefore, is not to be taken in a limiting sense, and the scope of the disclosure is defined by the appended claims.

In the following description, flaws refer to surface flaws such as tin points, sticky dirt, scratches and the like, which are distributed at the surface of the substrate, as well as internal flaws such as bubbles, stones, knots and the like, which are distributed inside the substrate.

Figure 1:
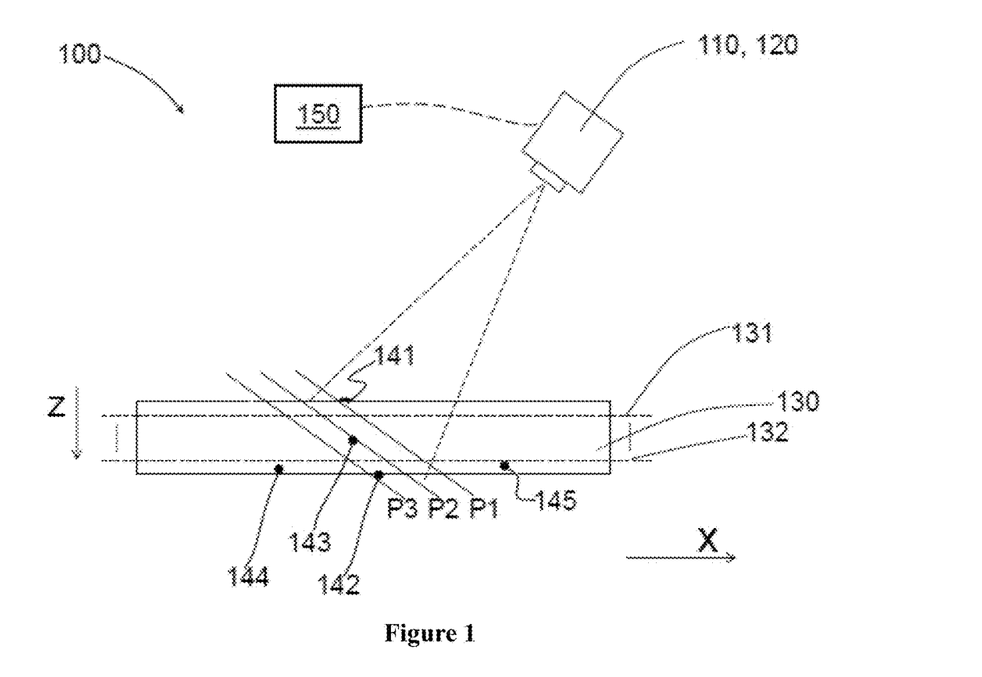
FIG. 1 is a schematic diagram of an optical device 100 for detecting an internal flaw of a transparent substrate according to an embodiment of the present disclosure.

Referring to FIG. 1, an exemplary optical device 100 for detecting an internal flaw of a transparent substrate includes: a first detection unit 110 configured to detect a glass substrate 130 at a predetermined low resolution; a second detection unit 120 configured to detect the glass substrate 130 at a predetermined high resolution (the first detection unit 110 and the second detection unit 120 are illustrated as one component for purpose of clarity); and a processor 150 configured to determine a portion of the flaws detected by the first detection unit 110 as flaws to be detected by the second detection unit 120, and to determine a type of the flaw based on an image for the substrate imaged by the second detection unit 120.

Figure 2:
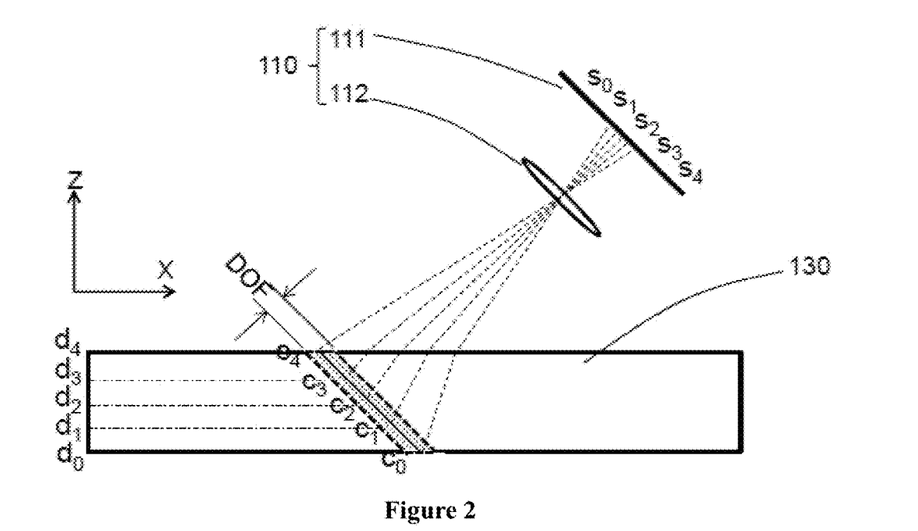
FIG. 2 illustrates an exemplary first detection unit 110 for detecting at a predetermined low resolution.

Specifically, referring to FIG. 2, an exemplary first detection unit 110 includes a first photosensitive element 111 and a first lens 112 between the substrate 130 and the first photosensitive element 111. As illustrated in FIG. 2, a photosensitive surface of the first photosensitive element 111 is inclined relative to the substrate 130, and a principal plane of the first lens 112 is parallel to the photosensitive surface of the first photosensitive element 111. Therefore, an object plane is inclined relative to the substrate 130.

Figure 3:
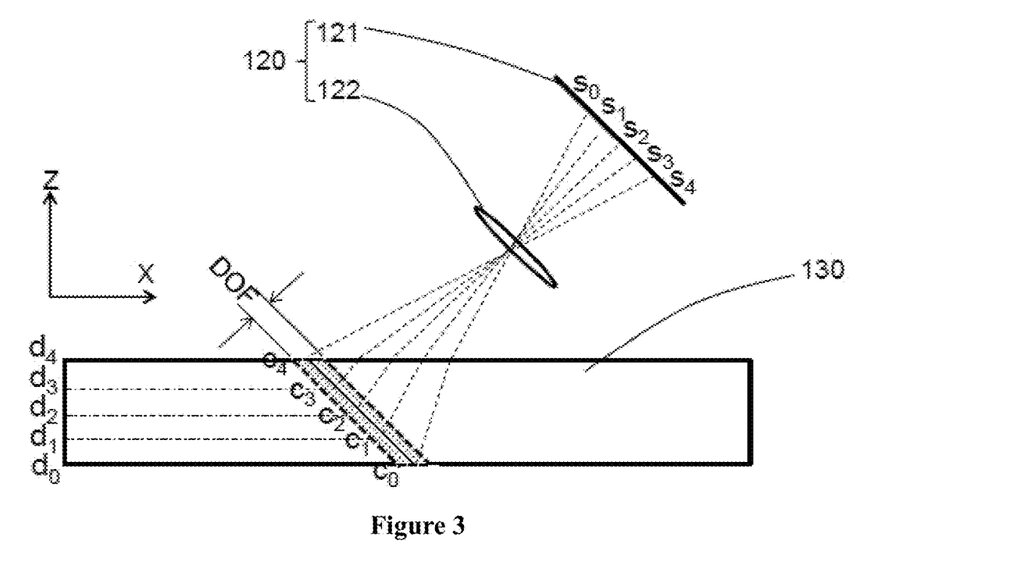
FIG. 3 illustrates an exemplary second detection unit 120 for detecting at a predetermined high resolution.

Referring to FIG. 3, an exemplary second detection unit 120 includes a second photosensitive element 121 and a second lens 122 between the substrate 130 and the second photosensitive element 121.

In FIG. 1, the processor 150 is connected with the photosensitive elements of the detection unit 110 and the detection unit 120 to acquire the detected data. Specifically, the processor 150 may be implemented by a computer, or may be implemented by other hardware such as a microcontroller or a digital signal processing unit (DSP). The processor 150 may also be implemented by connecting the computer with other hardware device, such as a graphics processing board, a graphics processing unit (GPU).

It should be noted that FIG. 2 illustrates only an exemplary construction of the first detection unit. In order to make the object plane to be inclined relative to the substrate, a first detection unit 190 illustrated in FIG. 4 may also be employed. In the first detection unit 190, a principal plane of a first lens 192 is parallel to the substrate 130, and there is an angle between a photosensitive surface of a first photosensitive element 191 and the principal plane of the first lens 192, therefore the object plane is inclined relative to the substrate 130.

Figure 9:
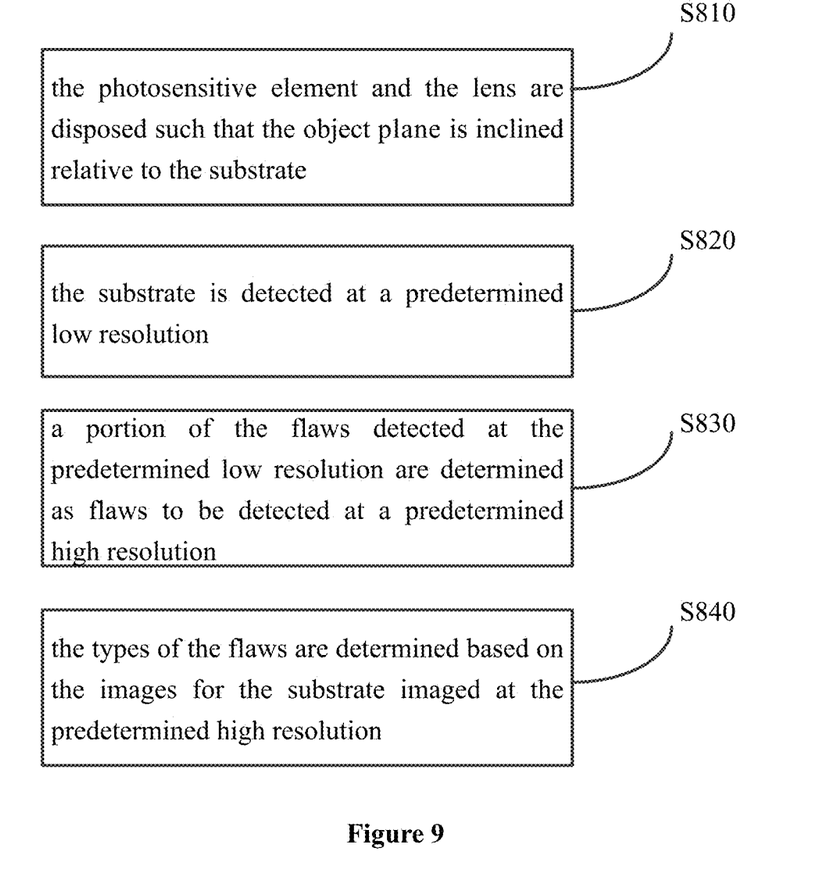
FIG. 9 illustrates a flowchart of a method for detecting an internal flaw of a transparent substrate according to an embodiment of the present disclosure.

The application of the optical device 100 is described in conjunction with the flowchart illustrated in FIG. 9.

In step S810, the first photosensitive element 111 and the first lens 112 are disposed such that an object plane is inclined relative to the substrate 130.

In step S820, the substrate 130 is detected at a predetermined low resolution by the first detection unit 110. Specifically, the optical device 100 may be fixed, and the glass substrate 130 may move along a direction of the coordinate X illustrated in FIG. 2. In this way, flaws of the substrate 130 are detected in the X direction. In the low-resolution detection, the detected flaws include surface flaws (such as sticky dirt, scratches and tin point, etc.) and internal flaws (such as bubbles and stones, etc.).

In step S830, the processor 150 determines a portion of the flaws detected at the predetermined low resolution as flaws to be detected at a predetermined high resolution. The portion of the flaws may include only flaws suspected to be bubbles and stones, or only flaws suspected to be stones, or all the internal flaws other than the surface flaws. This is determined depending on the actual requirement of the efficiency and accuracy of the detection, the detailed operation of step S830 is described hereinafter.

In step S840, the portion of the flaws of the substrate 130 are detected at the predetermined high resolution by the second detection unit 120, to obtain the detailed information about the flaws and to determine the types of the flaws.

The advantages of the optical device 100 are described as follows.

Specifically, the processor 150 determines only a portion of the flaws detected by the first detection unit 110 (for example, flaws including only flaws suspected to be bubbles and stones) as flaws to be detected by the second detection unit 120, therefore avoiding identifying the details of all the detected flaws one by one to determine the types of the flaws. Therefore, the optical device 100 has a relatively high detection efficiency.

Furthermore, since the substrate 130 is detected at a low resolution firstly, a photosensitive element with fewer number of pixels may be used to ensure the width of the whole substrate 130 (the width direction Y in FIG. 2 is the direction perpendicular to the plane of the paper, i.e., perpendicular to the longitudinal direction X along which the substrate moves relative to the photosensitive element) being covered by the field of view. Therefore, the optical device has a relatively low cost. For example, the number of pixels of a photosensitive element is 512*512. It is desired that all the flaws in the width direction are detected in one time movement of the substrate 130 in the X direction. For a substrate 130 with a width of 0.1 m, at least 200 such photosensitive elements are required if a high-resolution detection of 1 μm/px resolution is performed. Compared with the conventional methods, the optical device 100 first performs a low-resolution detection, for example, at a resolution of 5 μm/px (at which bubbles of 10 μm in size can be detected), only 40 such photosensitive elements are required to ensure that all the flaws in the width direction are detected in one time movement of the substrate 130.

Furthermore, the object plane is inclined relative to the substrate 130 in the low-resolution detection, this arrangement allows flaws (such as flaws 141, 142, 143, 144 and 145 at different positions of the substrate 130 in the thickness direction illustrated in FIG. 1) at different positions of the substrate 130 in the thickness direction to be imaged by the first detection unit 110. Therefore, in the low-resolution detection, it is only required that the photosensitive element moves relative to the substrate in the longitudinal direction (X), and it is not necessary for the photosensitive element to move relative to the substrate in a thickness direction (Z) to find out flaws at different positions of the substrate in the thickness direction (Z). The detection efficiency is further improved.

Figure 5:
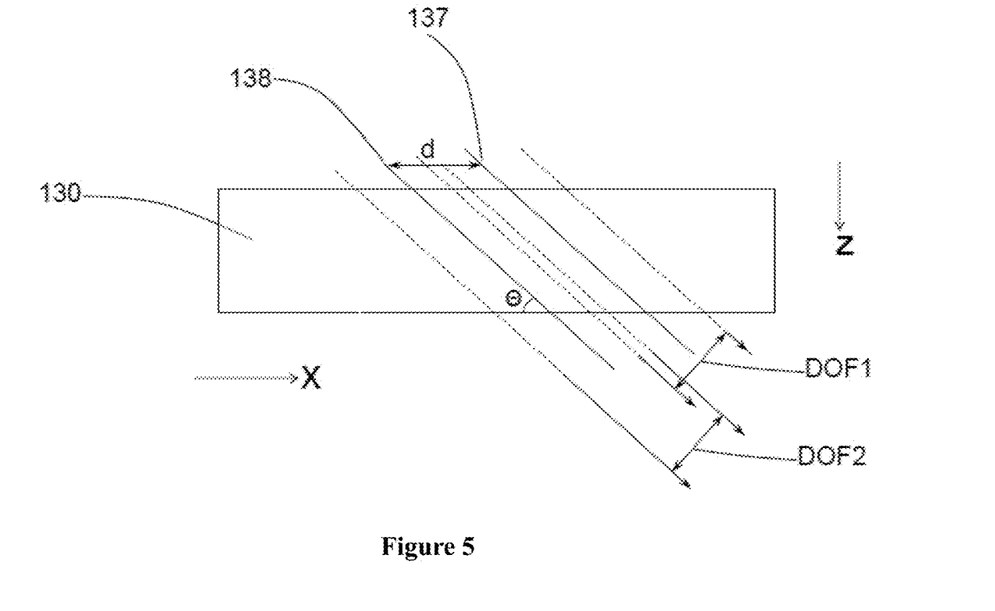
FIG. 5 illustrates a moving distance of the glass corresponding to two adjacent frames.

Moreover, as illustrated in FIG. 2, in the low-resolution detection, since the magnification of the first detection unit 110 is lower, the depth of field (DOF) is greater. The beneficial effect brought by this is allowing the substrate 130 to move relative to the detection unit 110 at a faster speed without missing a certain flaw between two adjacent frames. The detection efficiency is further improved. Specifically, reference is made to FIG. 5, which illustrates object planes 137, 138 corresponding to two adjacent frames with depth of fields DOF1 and DOF2 respectively (DOF1=DOF2). The angle between the object plane and the substrate 130 is θ. The moving distance of the glass between the two adjacent frames is d. It is required that d≤DOF. Assuming that the maximum frame rate of the photosensitive element is Rmax, the moving speed v should meet the following formula:

v≤Rmax*DOF/sin θ, so as to ensure not missing a flaw. Therefore, given the same frame rate, the larger the depth of field is, the faster the moving speed of the substrate is allowed.

The exemplary implementations of the high-resolution detection and the low-resolution detection are described below.

In an embodiment, the high-resolution detection and the low-resolution detection are implemented by changing the magnification.

Specifically, referring to FIG. 2, the first detection unit 110 of the optical device 100 is an area array CCD, which includes multiple rows of pixels arranged along the directions of S0, S1, S2, S3 and S4 (which is parallel to the width direction Y of the substrate). These pixels are different in height in direction Z for acquiring images for different zones c0, c1, c2, c3 and c4 in the substrate 130 at the thicknesses d0, d1, d2, d3 and d4, respectively.

It should be noted that FIG. 2 illustrates only five rows of pixels, those skilled in the art will appreciate that, the density of the pixels is determined depending on the desired resolution in the thickness direction. Photosensitive elements with more number of rows may be employed to achieve a high resolution in the thickness direction.

It is further noted that the construction of the first photosensitive element 111 is not limited thereto. In an embodiment, the first photosensitive element 111 includes multiple linear array CCDs. In another embodiment, the first photosensitive element 111 is a CMOS sensor.

Still referring to FIG. 2, the first detection unit 110 of the optical device 100 further includes a first lens 112. The first lens 112 is disposed such that the magnification of the first detection unit 110 is 1.

Referring to FIG. 3, the construction of the second photosensitive element 121 of the second detection unit 120 is the same as the construction of the first photosensitive element 111 of the first detection unit 110, both the first photosensitive element 111 and the second photosensitive element 121 include multiple rows of pixels arranged along the directions of S0, S1, S2, S3 and S4. The difference between the second detection unit 120 and the first detection unit 110 is that the positional relationship between the object and the image for the object is changed. The second lens 122 is disposed such that the magnification of the second detection unit 120 is 5.

Therefore, in an embodiment, for a glass substrate with a width of 0.1 m, the substrate is scanned at a low-resolution (e.g., 5 μm/pixel) using 40 first photosensitive elements 111 with 512*512 pixels (the pixel size of the photosensitive element 111 is 5 μm) arranged along the width direction of the substrate in conjunction with the first lens 112 to find out flaws of 10 μm or above in size. In the high-resolution scanning (e.g., 1 μm/pixel), the 40 first photosensitive elements 111 with 512*512 pixels are still used, however the first lens 112 is replaced with the lens 122, to acquire the detailed characters of a portion of the flaws.

It should be noted that in other embodiments, the magnification may be changed by using a fixed-focus lens. In other embodiments, the magnification may be changed by using a zoom lens.

Figure 4:
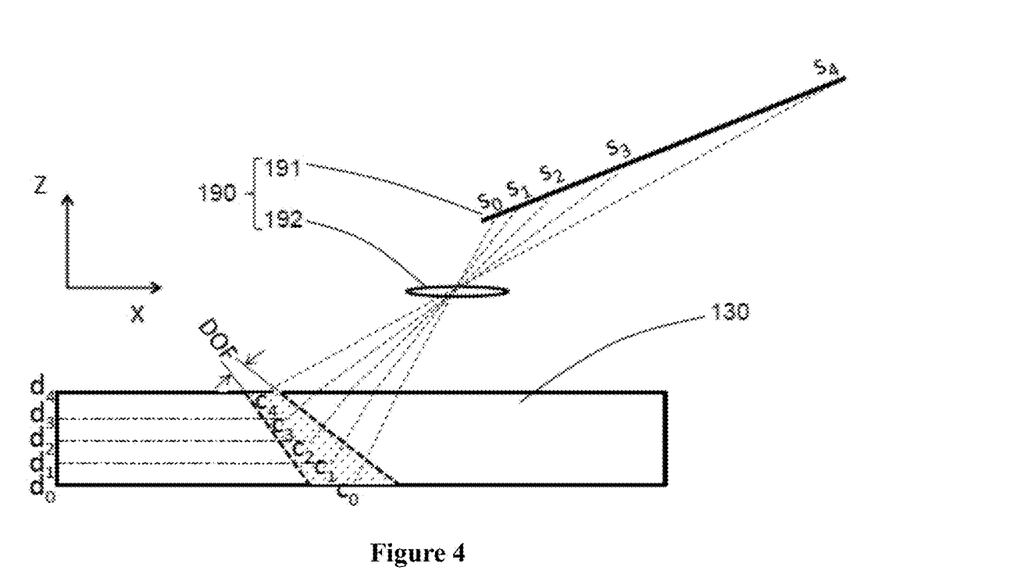
FIG. 4 illustrates another exemplary first detection unit 190 for detecting at a predetermined low resolution.

It is further noted that, in FIGS. 2 to 4, the lens 112 and the lens 122 are illustrated as spherical mirrors only for clarity. In practice, the lens may be a lens group, or a Diffractive Optical Element (abbreviated as DOE), or a Microlens array.

In another embodiment, the low-resolution detection and the high-resolution detection are implemented by changing the pixel size of the photosensitive elements. For example, in both the low-resolution detection and the high-resolution detection, the magnification is not changed, which is 5×. In the low-resolution detection, a camera with a pixel size of 25 μm is used. The image for a 10 μm flaw imaged at the photosensitive surface of the first photosensitive element 111 is 50 μm in size, which is approximately equal to two pixels in size, therefore the 10 μm flaw can be identified. In the high-resolution detection, a camera with a pixel size of 5 μm is used. The image for a 10 μm flaw imaged at the photosensitive surface of the second photosensitive element 121 is 50 μm, which is approximately equal to ten pixels in size, and the high-resolution detection may be used to acquire the detailed character of the flaw.

In the case of the conventional detection methods which do not distinguish between the high-resolution detection and the low-resolution detection, a high-resolution detection unit is used throughout the whole detection. If a detection unit with a resolution of 1 μm/px is used, 100,000 such pixels are required to cover the substrate of 0.1 m in width. In contrast, according to the method of the present disclosure, a detection unit with a resolution of 5 μm/px is used in the low-resolution detection. As a result, only 20,000 such pixels are required to cover the substrate of 0.1 m in width.

It should be noted that, the way to implement the high-resolution detection and the low-resolution detection is not limited to the above-described embodiments. In an embodiment, the focal length is changed by attaching the lens with a lens-adaptor ring without replacing the photosensitive element and the lens.

It is further noted that, the second photosensitive element 121 and the second lens 122 are illustrated in FIG. 3 as being inclined relative to the substrate 130. In other embodiments, the second photosensitive element 121 and the second lens 122 may also be disposed to be parallel to the substrate, because the second detection unit 120 is used to detect the details of the flaws rather than searching for potential flaws.

How the processor 150 determines a portion of the flaws detected by the first detection unit 110 as flaws to be detected by the second detection unit 120 is described below.

In an embodiment, the processor 150 determines whether a flaw is the flaw to be detected by the second detection unit 120 based on a position of the flaw in the thickness direction.

Figure 7:
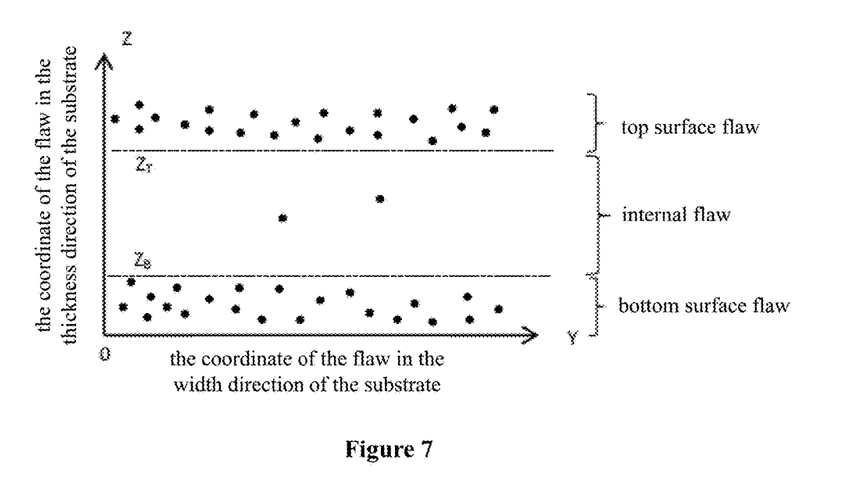
FIG. 7 exemplarily illustrates a distribution of the flaws detected by the first detection unit 110 in the substrate in the thickness direction.

Specifically, referring to FIG. 1, the glass substrate 130 moves along the X coordinate direction. During the movement, the detection unit 110 focuses on multiple inclined planes in the substrate 130. FIG. 1 illustrates three inclined planes P1, P2 and P3. The flaws 141,143 and 142 are clearly focused when the inclined planes P1, P2 and P3 are focused, respectively. The position of the flaw 143 in the substrate 130 in the thickness direction is determined based on a position of a pixel to which the flaw 143 corresponds in the image with an optimum sharpness. FIG. 7 illustrates a distribution of the flaws detected by the first detection unit 110 of the optical device 100. Based on the distribution, the flaws in the thickness direction of the glass, the coordinate of which are between ZB and ZT, are determined as the internal flaws. Since the position of the flaw 143 is between ZB and ZT, the flaw 143 is considered as an internal flaw. Since the positions of the flaws 141 and 142 are not between ZB and ZT, the flaws 141 and 142 are considered as the surface flaws.

Figure 6:
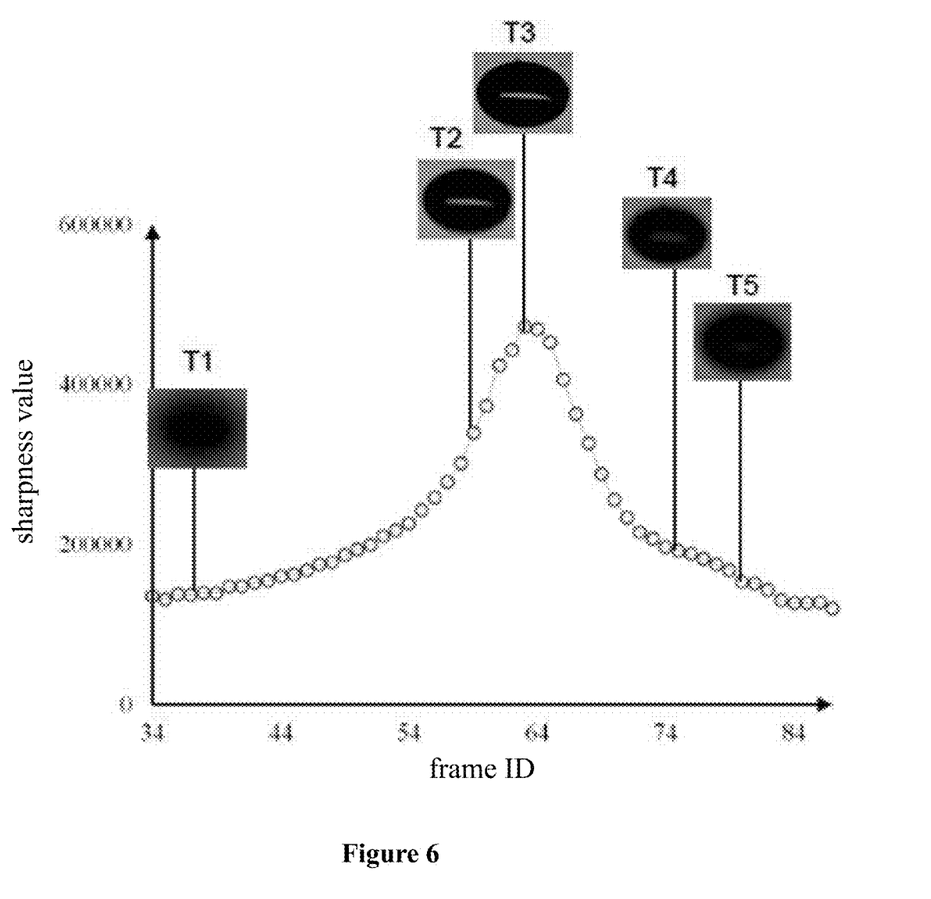
FIG. 6 illustrates a sequence of images for a flaw 143 imaged by the first detection unit 110, where the vertical coordinate represents a sharpness value and the horizontal coordinate represents a frame ID.

More specifically, in order to determine an image for one flaw with the optimum sharpness, in an embodiment, the first processor 150 acquires a sequence of images for one flaw imaged by the first detection unit 110, such as the sequence of images including multiple frames of images T1, T2, T3, T4 and T5, as illustrated in FIG. 6. The sequence of images includes at least three images imaged at three successive time instants respectively (for example, T3 and the images of the previous frame and the next frame, as illustrated in FIG. 6), wherein the sharpness value of the image imaged at the intermediate time instant T3 (with an frame ID 64) is higher than the sharpness values of the images imaged at the other time instants (with frame IDs 63 and 65). Therefore, the processor 150 determines T3 as the image for the one flaw with the optimum sharpness imaged by the first detection unit, and determines a position of the flaw in the substrate in the thickness direction based on the position of the pixel to which the flaw corresponds in the image.

The above embodiments are exemplary only, the at least three images imaged at three successive time instants respectively are not necessary. And it is not necessary for the processor to detect the at least three images imaged at three successive time instants respectively and to determine the image imaged at the intermediate time instant as the image with the optimum sharpness. In an embodiment, the processor determines an image with a highest sharpness value in a sequence of images for one flaw as the image with the optimum sharpness without judging whether the sharpness values of the two adjacent images are lower. Although such an approach may misdetermine the positions of occasional flaws in the thickness direction (for example, for occasional flaws which are not clearly focused throughout the movement of the substrate), the determination on the positions of most flaws in the thickness direction is correct.

It should be noted that the position, where a flaw is located in the thickness direction of the substrate for determining the flaw as a flaw to be detected at a high resolution, is set depending on the interested type of flaw and experiences. For example, the interested type of flaw is closed bubble. FIG. 7 illustrates a distribution of flaws detected by the first detection unit 110 of the optical device 100, and the flaws the position of which in the thickness direction of the glass being between ZB and ZT are determined as flaws to be detected at the high resolution. As illustrated in FIG. 7, only a small number of flaws are considered as the flaws required to be detected at the high resolution to determine the types of the flaws.

Figure 8:
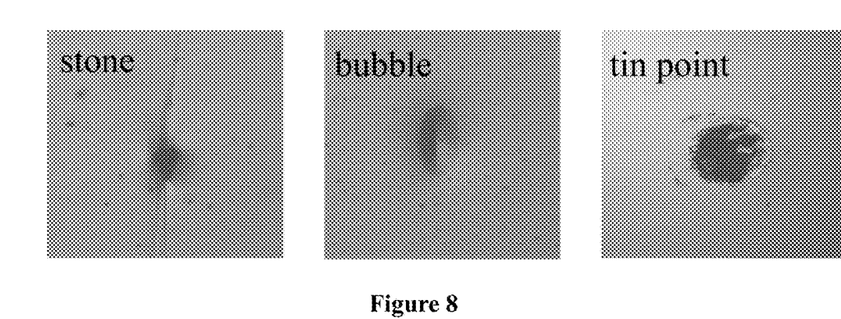
FIG. 8 illustrates images for several different types of flaws imaged at the low resolution.

It is further noted that whether the flaws detected at the low resolution are further required to be detected at the high resolution may be determined based on other criteria, for example, the morphology of the flaw. FIG. 8 illustrates images for flaws imaged at a resolution of 5 μm/px, which shows a stone, a bubble and a tin point from left to right respectively. As can be seen that the stone, the bubble and the tin point may be identified even at the low resolution of 5 μm/px. Therefore, by filtering the morphology of the flaws, the flaws requiring further detection at the high resolution are only a small portion of the flaws detected at the low resolution.

It is further noted that whether a flaw detected at the low resolution is further required to be detected at the high resolution may be determined based on the position of the flaw in the thickness direction of the substrate in combination with the morphology of the flaw.

It should be noted that the specific values of the above predetermined low resolution and the predetermined high resolution are set depending on the actual requirement of the efficiency, the cost, the accuracy of the detection. For example, in a cost-sensitive application, the predetermined low resolution may be set lower, such as 30 μm/px, to reduce the number of the photosensitive elements, as long as the detection accuracy is acceptable. In an application that requires high accuracy, the predetermined high resolution may be set higher, such as 1 μm/px, to find out more details of the flaws. The overall cost of the optical device 100 is not affected much even if the cost of such a photosensitive element (with a resolution of 1 μm/px) is high, because the low-resolution photosensitive elements are used to perform the low-resolution detection and only one single high-resolution photosensitive element is used to perform the high-resolution detection.

The light source employed during the detection is not described above. Those skilled in the art will appreciate that during the detection of the flaws, a light source, such as a bright field transmission light source, a bright field reflection light source and the like, is typically used to illuminate the substrate to acquire images clearly. The optical device and method for detecting a flaw of a transparent substrate according to the embodiments of the present disclosure may also work with a light source. In addition, in the high-resolution detection, in order to identify the details, the second detection unit may further work with light sources of different illumination modes which are not described herein for conciseness. The optical device or the detection method working with a light source or light sources of different illumination modes falls within the protection scope of the present disclosure.

The above description takes of the glass substrate as an example, the optical device and method according to the embodiments of the present disclosure may also be used to detect internal flaws of other transparent substrates, for example, to detect the Polymethylmethacrylate (PMMA).

It should be noted that the above described embodiments are given for describing rather than limiting the present disclosure, and it is to be understood by those skilled in the art that modifications and variations may be made to the disclosure without departing from the spirit and scope of the present disclosure. Such modifications and variations are considered to be within the scope of the present disclosure and the appended claims. The protection scope of the present disclosure is defined by the appended claims. In addition, any of the reference numerals in the claims should not be interpreted as a limitation to the present disclosure. Use of the verb "comprise" and its conjugations does not exclude the presence of elements or steps other than those stated in a claim. The indefinite article "a" or "an" preceding an element or step does not exclude the presence of multiple such elements or steps.

The invention claimed is:

1. An optical device for detecting an internal flaw of a transparent substrate, comprising:
   a first detection unit configured to detect the substrate at a predetermined low resolution, wherein the first detection unit comprises a first photosensitive element and a first lens between the substrate and the first photosensitive element, and the first photosensitive element and the first lens are disposed such that an object plane is inclined relative to the substrate;
   a second detection unit configured to detect the substrate at a predetermined high resolution, wherein the second detection unit comprises a second photosensitive element and a second lens between the substrate and the second photosensitive element; and
   a processor configured to: determine a portion of the flaws detected by the first detection unit as flaws to be detected by the second detection unit, and determine a type of the flaw based on an image for the substrate imaged by the second detection unit, the processor is further configured to determine a position of the flaw in the substrate in a thickness direction based on a position of a pixel where the flaw is imaged on the first photosensitive element when the image for the flaw imaged by the first detection unit has an optimum sharpness, so as to determine whether the flaw is a flaw to be detected by the second detection unit.

2. The optical device according to claim 1, wherein a photosensitive surface of the first photosensitive element is inclined relative to the substrate, and a principal plane of the first lens is parallel to the photosensitive surface of the first photosensitive element.

3. The optical device according to claim 1, wherein a magnification of the second detection unit is higher than a magnification of the first detection unit, and the second photosensitive element and the first photosensitive element have the same structure.

4. The optical device according to claim 1, wherein a pixel size of the second photosensitive element is smaller than a pixel size of the first photosensitive element, and a construction of the second lens is the same as a construction of the first lens.

5. The optical device according to claim 1, wherein the second photosensitive element and the second lens are disposed such that an object plane is inclined relative to the substrate.

6. The optical device according to claim 1, wherein the first photosensitive element and the second photosensitive element comprise a CCD sensor or a CMOS sensor.

7. The optical device according to claim 1, wherein that the processor is further configured to: determine whether the flaw is a flaw to be detected by the second detection unit based on a morphology of the flaw in the image for the flaw imaged by the first detection unit.

8. The optical device according to claim 1, wherein the substrate is glass.

9. A method for detecting an internal flaw of a transparent substrate, comprising:
   a. disposing a photosensitive element and a lens such that an object plane is inclined relative to the substrate;

b. detecting the substrate at a predetermined low resolution;
c. determining a portion of the flaws detected at the predetermined low resolution as flaws to be detected at a predetermined high resolution; and
d. determining a type of the flaw based on an image for the substrate imaged at the predetermined high resolution,
wherein step c comprises: determining a position of the flaw in the substrate in a thickness direction based on a position of a pixel where the flaw is imaged on the photosensitive element when the image for the flaw imaged at the predetermined low resolution has an optimum sharpness, so as to determine whether the flaw is a flaw to be detected at the predetermined high resolution.

10. The method according to claim 9, wherein step c comprises: acquiring a sequence of images for one flaw imaged at the predetermined low resolution, the sequence of images comprising at least three images imaged at three successive time instants respectively where a sharpness value of the image imaged at an intermediate time instant is higher than sharpness values of the images imaged at the other two time instants; and determining the image imaged at the intermediate time instant as the image for the one flaw with an optimum sharpness imaged at the predetermined low resolution.

* * * * *